United States Patent
Tickner et al.

(10) Patent No.: US 7,153,976 B2
(45) Date of Patent: Dec. 26, 2006

(54) PURIFICATION PROCESS FOR AN AZABICYCLO[3.1.0]HEXANE COMPOUND

(75) Inventors: Derek L. Tickner, Waterford, CT (US); John J. Teixeira, Jr., Mystic, CT (US)

(73) Assignee: Pfizer Inc., New York, NY (US)

( * ) Notice: Subject to any disclaimer, the term of this patent is extended or adjusted under 35 U.S.C. 154(b) by 324 days.

(21) Appl. No.: 10/935,442

(22) Filed: Sep. 7, 2004

(65) Prior Publication Data

US 2005/0075387 A1 Apr. 7, 2005

Related U.S. Application Data

(60) Provisional application No. 60/509,088, filed on Oct. 6, 2003.

(51) Int. Cl.
*C07D 209/52* (2006.01)

(52) U.S. Cl. .................................................. 548/454
(58) Field of Classification Search ................ 548/454
See application file for complete search history.

(56) References Cited

U.S. PATENT DOCUMENTS 7,049,335 B1 * 5/2006 McHardy et al. ........... 514/412

FOREIGN PATENT DOCUMENTS

JP 08325228 * 12/1996

* cited by examiner

*Primary Examiner*—Taofiq Solola
(74) *Attorney, Agent, or Firm*—Gregg C. Benson; Arlene K. Musser

(57) ABSTRACT

A process for preparing azabicyclo[3.1.0]hexane compounds having reduced process-related impurities, e.g. 3-azabicyclo[3.1.0]hexane derivatives having reduced levels of etheric impurities, e.g. THF, is disclosed.

21 Claims, No Drawings

PURIFICATION PROCESS FOR AN AZABICYCLO[3.1.0]HEXANE COMPOUND

The entire disclosure of parent application 60/509,088 filed 10/06/03 is fully incorporated herein by reference thereto.

FIELD OF THE INVENTION

The invention relates to a process for preparing an azabicyclo[3.1.0]hexane compound whereby a reduction in impurities, especially process-related impurities, e.g. ethers, is obtained.

BACKGROUND OF THE INVENTION

Azabicyclo[3.1.0]hexane compounds have use as pharmaceuticals. For example, 3-azabicyclo[3.1.0]hexane derivatives can bind to opiate receptors such as mu, kappa and delta opioid receptors. This ability makes them useful in treating diseases modulated by opiate receptors such as irritable bowel syndrome, constipation, nausea, vomiting; and including pruritic dermatoses such as allergic dermatitis and atopy in animals and humans. Compounds that bind to opiate receptors have also been indicated in treating eating disorders, opiate overdoses, depression, smoking, and alcohol addition and dependence, sexual dysfunction, shock, stroke, spinal damage and head trama.

3-azabicyclo[3.1.0]hexane derivatives, their synthesis and use as opioid derivatives, are disclosed in WO 00/39089 and U.S. patent application Ser. No. 10/278,142, filed Oct. 22, 2002 entitled "3-Azabicyclo[3.1.0]hexane Derivatives."

Fabrication of azabicyclo[3.1.0]hexane compounds for pharmaceutical usage typically entails formation of a related salt. Oftentimes, however, an unwanted suspension of fine oil droplets is created during manufacture which adheres to the vessel, causing disruption of operations that can be particularly burdensome in large scale, bulk synthesis of such compounds. Ameliorating this is the use of select solvents such as tetrahydrofuran (THF) as a medium in which salt synthesis occurs. While THF redresses the oiling and adherence problem, it is often retained with the final azabicyclohexane product—by entrainment, for example—at levels that are unacceptable in a clinical use setting. Efforts to reduce the amount of THF, and indeed other process-related impurities, from the azabicyclo[3.1.0]hexane compound have met with only partial success, e.g. vacuum drying, employing a smaller particle size.

Thus there is a need for a process to prepare an azabicyclo [3.1.0]hexane compound having reduced impurities—particularly process-related impurities such as THF and the like—in amounts sufficient to permit clinical use, without breaking the salt to free base form and without adding undue steps to the preparation.

SUMMARY OF THE INVENTION

The invention is directed to such a process for preparing an azabicyclo[3.1.0]hexane compound having reduced impurities. The process comprises contacting a mixture containing an azabicyclo[3.1.0]hexane compound and at least one process-related impurity at a first concentration with an alcohol; and recovering from said mixture said azabicyclo[3.1.0]hexane compound having said at least one process-related impurity at a second concentration, said second concentration being less than said first concentration.

In a particular embodiment, a polar impurity is THF; preferably the second concentration, post processing, is acceptable for clinical use. A preferred azabicyclo[3.1.0]hexane is a 3-azabicyclo[3.1.0]hexane compound.

DETAILED DESCRIPTION OF THE INVENTION

Azabicyclo[3.1.0]hexane compound:

The term azabicyclo[3.1.0]hexane denotes compounds that are understood to the artisan. In one practice, azabicyclo [3.1.0]hexane compounds subject to the present process include those known in the art. In a preferred practice, the azabicyclo[3.1.0]hexane is a 3-azabicyclo[3.1.0]hexane compound, examples of which are disclosed in commonly-assigned patent application U.S. Ser. No. 10/278142 the contents of which are incorporated herein entirely.

Without limitation, a preferred 3-azabicyclo[3.1.0]hexane compound useful in the present invention has Formula I, below:

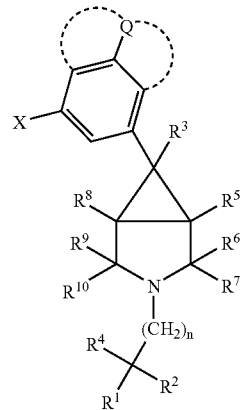

I wherein X is H, halogen, —OH, —CN, —$C_1$–$C_4$ alkyl substituted with from one to three halogen atoms, or —O($C_1$–$C_4$ alkyl), wherein the $C_1$–$C_4$ alkyl of —O($C_1$–$C_4$ alkyl) is optionally substituted with from one to three halogen atoms;

Q is halogen, —OH, —O($C_1$–$C_4$ alkyl), —$NH_2$, —NH ($C_1$–$C_4$ alkyl), —N($C_1$–$C_4$ alkyl)($C_1$–$C_4$ alkyl), —C(=O) $NH_2$, —C(=O)NH($C_1$–$C_4$ alkyl), —C(=O)N($C_1$–$C_4$ alkyl) ($C_1$–$C_4$ alkyl), —NHS(=O)$_2$H, or —NHS(=O)$_2$$R^{11}$;

or Q may form a 5 or 6 membered cycloalkyl or heterocycloalkyl ring with either carbon atom adjacent to the carbon atom to which it is attached, thereby forming a bicyclic fused ring system with the phenyl to which it is attached, wherein said heterocycloalkyl comprises from one to three hetero moieties selected from O, S, —C(=O), and N, and wherein said cycloalkyl or heterocycloalkyl optionally contains one or two double bonds;

$R^1$ and $R^2$ are, with the carbon to which they are attached, connected to form a $C_3$–$C_7$ cycloalkyl or a 4–7 membered heterocycloalkyl comprising from one to three hetero moieties selected from O, S, —C(=O), and N; and wherein said cycloalkyl or heterocycloalkyl optionally contains one or two double bonds; and wherein said cycloalkyl or heterocycloalkyl is optionally fused to a $C_6$–$C_{14}$ aryl or 5–14 membered heteroaryl group;

wherein said $C_3$–$C_7$ cycloalkyl or 4–7 membered heterocycloalkyl formed by $R^1$ and $R^2$ can each optionally be substituted by from one to three $R^{12}$ groups, and said optionally fused aryl or heteroaryl can each optionally independently be substituted with from one to six $R^{12}$ groups, wherein the $R^{12}$ groups are selected from $R^{13}$, $R^{16}$, —$C_1$–$C_4$ alkyl containing one or two unsaturated bonds, halogen, —$OR^{13}$, —$NO_2$, —CN, —$C_3$–$C_6$ cycloalkyl, —$NR^{13}R^{14}$, —$NR^{13}C(=O)R^{14}$, —$C(=O)NR^{13}R^{14}$, —OC(=O)$R^{13}$, —$C(=O)OR^{13}$, —$C(=O)R^{13}$, —$NR^{13}C(=O)OR^{14}$, —$NR^{13}C(=O)NR^{14}R^{15}$, —$NR^{13}S(=O)_2R^{14}$, and —$S(=O)_2R^{13}$;

$R^3$ is $C_1$–$C_4$ alkyl, wherein said $C_1$–$C_4$ alkyl optionally contains one or two unsaturated bonds;

$R^4$ is —$C_1$–$C_4$ alkyl which may optionally contain one or two unsaturated bonds, —OH, —CN, $NO^2$, —$OR^{16}$, —$NH_2$, —$NHR^{16}$, —$NR^{16}R^{17}$, or —$NHC(=O)R^{16}$;

$R^5$ and $R^8$ are each independently H or methyl;

$R^6$, $R^7$, $R^9$ and $R^{10}$ are H;

$R^{11}$ is selected from $C_1$–$C_4$ alkyl, —($C_1$–$C_4$ alkylene)—O—($C_1$–$C_4$ alkyl), 4-(1-methylimidazole), —($C_1$–$C_4$ alkylene)—$NH_2$, —($C_1$–$C_4$ alkylene)—NH($C_1$–$C_4$ alkyl), —($C_1$–$C_4$ alkylene)-N($C_1$–$C_4$ alkyl)($C_1$–$C_4$ alkyl);

each $R^{13}$, $R^{14}$, and $R^{15}$ is independently selected from H, $R^{16}$, $C_1$–$C_4$ alkyl, halogen, —OH, —SH, —$NH_2$, —NH($C_1$–$C_4$ alkyl), —N($C_1$–$C_4$ alkyl)($C_1$–$C_4$ alkyl), —O($C_1$–$C_4$ alkyl), —S($C_1$–$C_4$ alkyl), —CN, —$NO_2$, —$C(=O)$($C_1$–$C_4$ alkyl), —$C(=O)$OH, —$C(=O)O$($C_1$–$C_4$ alkyl), —NHC$(=O)$($C_1$–$C_4$ alkyl), —$C(=O)NH_2$, and —$C(=O)N$($C_1$–$C_4$ alkyl)($C_1$–$C_4$ alkyl), or $R^{13}$ and $R^{14}$ when in —$NR^{13}R^{14}$, may optionally be connected to form a 4 to 6 membered heterocycloalkyl or heteroaryl group, which heterorayl group optionally comprises from 1 to 3 further hetero moieties selected from N, S, O and —$C(=O)$;

each $R^{16}$ and $R^{17}$ is independently selected from $C_1$–$C_4$ alkyl, $C_6$–$C_{14}$ aryl and 5–14 membered heteroaryl, wherein said heteroaryl comprises from one to three hetero moieties selected from O, S, —$C(=O)$, and N, and wherein said aryl and heteroaryl are optionally substituted with from one to three substituents selected from $C_1$–$C_4$ alkyl optionally containing one or two unsaturated bonds, halogen, —OH, —SH, —$NH_2$, —NH($C_1$–$C_4$ alkyl), —N($C_1$–$C_4$ alkyl)($C_1$–$C_4$ alkyl), —O($C_1$–$C_4$ alkyl), —S($C_1$–$C_4$ alkyl), —CN, —$NO_2$, —$C(=O)$($C_1$–$C_4$ alkyl), —$C(=O)$OH, —$C(=O)O$($C_1$–$C_4$ alkyl), —NHC$(=O)$($C_1$–$C_4$ alkyl), —$C(=O)NH_2$, and —$C(=O)N$($C_1$–$C_4$ alkyl)($C_1$–$C_4$ alkyl); and n is an integer selected from zero, 1, 2, 3, 4, and 5;

and for pharmaceutically acceptable salts thereof.

In one embodiment, the process of the invention involves compounds of Formula I wherein $R^3$ is methyl, ethyl, or straight-chain propyl. In another embodiment, $R^3$ is methyl, ethyl, isopropyl or straight-chain propyl. In a preferred embodiment, $R^3$ is ethyl.

In another embodiment, in the compounds of Formula I, $R^4$ is —CN, —$NO_2$, —OH, —$NH_2$, —O($C_1$–$C_4$ alkyl), —($C_1$–$C_4$ alkylene)—OH, —NHC$(=O)$($C_1$–$C_4$ alkyl), —NH($C_1$–$C_4$ alkyl), or —N($C_1$–$C_4$ alkyl)($C_1$–$C_4$ alkyl).

In another embodiment, in the compounds of Formula I, $R^4$ is —CN, —$NO_2$, —OH, —$OCH_3$, —$CH_2OH$, —$NH_2$, or —NHC$(=O)CH_3$. In another embodiment $R^4$ is —OH, —$OCH_3$, —$CH_2OH$, —$NH_2$, or —NHC$(=O)CH_3$. In a preferred embodiment, $R^4$ is —OH.

In another embodiment, in the compounds of Formula I, Q is halogen, —OH, —O($C_1$–$C_4$ alkyl), —$NH_2$, —NH($C_1$–$C_4$ alkyl), —N($C_1$–$C_4$ alkyl)($C_1$–$C_4$ alkyl), —$C(=O)NH_2$, —$C(=O)NH$($C_1$–$C_4$ alkyl), —$C(=O)N$($C_1$–$C_4$ alkyl)($C_1$–$C_4$ alkyl), —NHS$(=O)_2H$, or —NHS$(=O)_2R^{11}$ In another embodiment, in the compounds of Formula I, Q is F, —OH, —$C(=O)NH_2$, —$NH_2$, —NHS$(=O)_2CH_3$, —NHS$(=O)_2CH_2CH_3$, —NHS$(=O)_2CH_2CH_2CH_3$, —NHS$(=O)_2CH(CH_3)(CH_3)$, —NHS$(=O)_2CH_2CH_2OCH_3$, or —NHS$(=O)_2$(4-(1-methylimidazole)). In another embodiment, Q is F, —OH, —$C(=O)NH_2$, —NHS$(=O)_2CH_3$, —NHS$(=O)_2CH_2CH_2OCH_3$, or —NHS$(=O)_2$(4-(1-methylimidazole)).

In another embodiment, in the compounds of Formula I, X is H, F, —OH, —$C(=O)NH_2$, or —CN. In another embodiment, X is H, F, —OH, or —CN.

In another embodiment, in the compounds of Formula I, Q is F, —OH, —$C(=O)NH_2$, —NHS$(=O)_2CH_3$, —NHS$(=O)_2CH_2CH_2OCH_3$, or —NHS$(=O)_2$(4-1-methylimidazole)) and X is H, F, —OH, or —CN.

In another embodiment, in the compounds of Formula I, n is an integer selected from zero, one, two, or three. Preferably, n is an integer selected from one, two or three.

In another embodiment, in the compounds of Formula I, $R^1$ and $R^2$, with the carbon to which they are attached, are connected to form a cyclopropyl, cyclobutyl, cyclopentyl, or cyclohexyl group, each optionally substituted with one or two $R^{12}$ groups.

In another embodiment, in the compounds of Formula I, $R^1$ and $R^2$, with the carbon to which they are attached, are connected to form a cyclopentyl group, optionally substituted with from one or two $R^{12}$ groups. In one embodiment, the cyclopentyl group formed by $R^1$ and $R^2$ is not substituted with an $R^{12}$ group.

In another embodiment, in the compounds of Formula I, $R^1$ and $R^2$, with the carbon to which they are attached, are connected to form a cyclohexyl group optionally substituted with one or two $R^{12}$ groups. In one embodiment, the cyclohexyl group formed by $R^1$ and $R^2$ is not substituted with an $R^{12}$ group.

In another embodiment, in the compounds of Formula I, the ring formed by $R^1$ and $R^2$, for example a cyclopentyl or cyclohexyl ring, is fused to a benzene ring, and the ring formed by $R^1$ and $R^2$ and the benzene ring are each optionally substituted as recited above. In a more specific embodiment, the benzene ring and/or the ring formed by $R^1$ and $R^2$ are each optionally substituted with one or two $R^{12}$ groups. In one embodiment, the benzene is not substituted with any $R^{12}$ group. In another more specific embodiment, $R^1$ and $R^2$ form a cyclohexyl group, which cyclohexyl group is fused to a benzene ring, or $R^1$ and $R^2$ form a cyclopentyl group, which cyclopentyl group is fused to a benzene ring. In either case (cylopentyl fused to benzene or cyclohexyl fused to benzene) said cyclopentyl or cyclohexyl and/or the fused benzene ring are each optionally substituted with one or two $R^{12}$ as recited above. In another embodiment, the cyclohexyl or cyclopentyl group that is fused to the benzene is not substituted with any $R^{12}$ group.

In each of the aforementioned embodiments, when an $R^{12}$ substituent is present, it is in one embodiment a —CN or halogen, for example a fluoro group.

In another embodiment, in the compounds of Formula I, when $R^1$ and $R^2$ form a cyclohexyl or cyclopentyl, the cyclohexyl or cyclopentyl are optionally fused to a benzene ring, and $R^3$ is methyl, ethyl, isopropyl or straight-chain propyl. In another such embodiment $R^3$ is methyl, ethyl or straight-chain propyl. In a preferred embodiment, $R^3$ is ethyl.

In another embodiment, in the compounds of Formula I, when $R^1$ and $R^2$ form a cyclohexyl or cyclopentyl, the cyclohexyl or cyclopentyl are optionally fused to a benzene ring, and $R^4$ is —OH, —$OCH_3$, —$CH_2OH$, —$NH_2$, or —NHC(=O)CH$_3$. In another such embodiment R$^4$ is —CN, —NO$_2$, —OH, —OCH$_3$, —CH$_2$OH, —NH$_2$, or —NHC(=O)CH$_3$. In another such embodiment R$^4$ is —CN, —NO$_2$, —OH, —NH$_2$, —O(C$_1$–C$_4$ alkyl), —(C$_1$–C$_4$ alkylene)—OH, —NHC(=O)(C$_1$–C$_4$ alkyl), —NH(C$_1$–C$_4$ alkyl), or —N(C$_1$–C$_4$ alkyl)(C$_1$–C$_4$ alkyl). In a preferred embodiment, R$^4$ is —OH.

In another embodiment, in the compounds of Formula I, when R$^1$ and R$^2$ form a cyclohexyl or cyclopentyl, the cyclohexyl or cyclopentyl are optionally fused to a benzene ring, and Q is F, —OH, —C(=O)NH$_2$, —NHS(=O)$_2$CH$_3$, —NHS(=O)$_2$CH$_2$CH$_2$OCH$_3$, or —NHS(=O)$_2$(4-(1-methylimidazole)). In another such embodiment Q is halogen, —OH, —O(C$_1$–C$_4$ alkyl), —NH$_2$, —NH(C$_1$–C$_4$ alkyl), —N(C$_1$–C$_4$ alkyl)(C$_1$–C$_4$ alkyl), —C(=O)NH$_2$, —C(=O)NH(C$_1$–C$_4$ alkyl), —C(=O)N(C$_1$–C$_4$ alkyl)(C$_1$–C$_4$ alkyl), —NHS(=O)$_2$H, or —NHS(=O)$_2$R$^{11}$. In another such embodiment, Q is F, —OH, —C(=O)NH$_2$, —NHS(=O)$_2$CH$_3$, —NHS(=O)$_2$CH$_2$CH$_3$, —NHS(=O)$_2$CH$_2$CH$_2$CH$_3$, —NHS(=O)$_2$CH(CH$_3$)(CH$_3$), —NHS(=O)$_2$CH$_2$CH$_2$OCH$_3$, or —NHS(=O)$_2$(4-(1-methylimidazole)).

In another embodiment of the invention, when R$^1$ and R$^2$ form a cyclohexyl or cyclopentyl, the cyclohexyl or cyclopentyl are optionally fused to a benzene ring, and X is H, F, —OH, —C(=O)NH$_2$, or —CN. In another such embodiment, X is H, F, —OH, or —CN.

In another embodiment, when R$^1$ and R$^2$ form a cyclohexyl or cyclopentyl, the cyclohexyl or cyclopentyl are optionally fused to a benzene ring, Q is F, —OH, —C(=O)NH$_2$, —NHS(=O)$_2$CH$_3$, —NHS(=O)$_2$CH$_2$CH$_2$OCH$_3$, or —NHS(=O)$_2$(4-1-methylimidazole)) and X is H, F, —OH, or —CN.

In another embodiment, when R$^1$ and R$^2$ form a cyclohexyl or cyclopentyl, the cyclohexyl or cyclopentyl are optionally fused to a benzene ring, and n is an integer selected from one, two, and three. In another such embodiment, n is an integer selected from one, two, and three, and Q is halogen, —OH, —O(C$_1$–C$_4$ alkyl), —NH$_2$, —NH(C$_1$–C$_4$ alkyl), —N(C$_1$–C$_4$ alkyl)(C$_1$–C$_4$ alkyl), —C(=O)NH$_2$, —C(=O)NH(C$_1$–C$_4$ alkyl), —C(=O)N(C$_1$–C$_4$ alkyl)(C$_1$–C$_4$ alkyl), —NHS(=O)$_2$H, or —NHS(=O)$_2$R$^{11}$.

In another embodiment, in the compounds of Formula I, R$^5$ and R$^8$ are both hydrogen.

Without limitation, examples of compounds of Formula I subject to the process of the present invention include:

Exo-N-(3-{6-ethyl-3-[3-(1-hydroxy-cyclohexyl)-propyl]-3-aza-bicyclo[3.1.0]hex-6-yl}-phenyl)-methanesulfonamide;

Exo-N-(3-{6-ethyl-3-[3-(1-hydroxymethyl-cyclopentyl)-propyl]-3-aza-bicyclo[3.1.0]hex-6-yl}-phenyl)-methanesulfonamide;

Exo-N-{3-[6-ethyl-3-(2-hydroxy-indan-2-ylmethyl)-3-aza-bicyclo[3.1.0]hex-6-yl]-phenyl}-methanesulfonamide;

Exo-1-{3-[6-(3,5-difluoro-phenyl)-6-ethyl-3-aza-bicyclo[3.1.0]hex-3-yl]-propyl}-cyclohexanol;

Exo-3-{6-ethyl-3-[3-(1-hydroxy-cyclohexyl)-propyl]-3-aza-bicyclo[3.1.0]hex-6-yl}-benzamide;

Exo-2-methoxy-ethanesulfonic acid (3-{6-ethyl-3-[3-(1-hydroxy-cyclohexyl)-propyl]-3aza-bicyclo[3.1.0]hex-6-yl}-phenyl)-amide;

Exo-3-[6-ethyl-3-(2-hydroxy-indan-2-ylmethyl)-3-aza-bicyclo[3.1.0]hex-6-yl]-5-fluoro-benzamide;

Exo-3-[6-ethyl-3-(2-hydroxy-indan-2-ylmethyl)-3-aza-bicyclo[3.1.0]hex-6-yl]-benzamide;

Exo-2-methoxy-ethanesulfonic acid {3-[6-ethyl-3-(2-hydroxy-indan-2-ylmethyl)-3-aza-bicyclo[3.1.0]hex-6-yl]-phenyl}-amide;

Exo-2-methoxy-ethanesulfonic acid [3-(6-ethyl-3-indan-2-ylmethyl-3-aza-bicyclo[3.1.0]hex-6-yl)-phenyl]-amide;

Exo-N-{3-[6-ethyl-3-(2-hydroxy-indan-2-ylmethyl)-3-aza-bicyclo[3.1.0]hex-6-yl]-5-fluoro-phenyl}-methanesulfonamide;

Exo-N-(3-{6-ethyl-3-[3-(1-hydroxy-cyclohexyl)-propyl]-3-aza-bicyclo[3.1.0]hex-6-yl}-5-fluoro-phenyl)-methanesulfonamide;

Exo-1-methyl-1H-imidazole-4-sulfonic acid {3-[6-ethyl-3-(2-hydroxy-indan-2-ylmethyl)-3-aza-bicyclo[3.1.0]hex-6-yl]-phenyl}-amide;

Exo-3-(6-ethyl-3-indan-2-ylmethyl-3-aza-bicyclo[3.1.0]hex-6-yl)-benzamide;

Exo-1-methyl-1H-imidazole-4-sulfonic acid [3-(6-ethyl-3-indan-2-ylmethyl-3-aza-bicyclo[3.1.0]hex-6-yl)-phenyl]-amide;

Exo-3-{6-ethyl-3-[3-(1-hydroxy-cyclohexyl)-propyl]-3-aza-bicyclo[3.1.0]hex-6-yl}-5-fluoro-benzamide;

Exo-1-methyl-1H-imidazole-4-sulfonic acid (3-{6-ethyl-3-[3-(1-hydroxy-cyclohexyl)-propyl]-3-aza-bicyclo[3.1.0]hex-6-yl}-phenyl)-amide;

Exo-3-{6-ethyl-3-[3-(1-hydroxy-cyclohexyl)-propyl]-3-aza-bicyclo[3.1.0]hex-6-yl}-phenol;

Exo-2-[6-ethyl-6-(3-hydroxy-phenyl)-3-aza-bicyclo[3.1.0]hex-3-ylmethyl]-indan-2-ol; and Exo-3-(6-ethyl-3-indan-2-ylmethyl-3-aza-bicyclo[3.1.0]hex-6-yl)-phenol;

and pharmaceutically acceptable salts thereof.

Exo-N-(3-{6-ethyl-3-[3-(1-hydroxy-cyclohexyl)-propyl]-3-aza-bicyclo[3.1.0]hex-6-yl}-phenyl)-methanesulfonamide citrate;

Exo-N-(3-{6-ethyl-3-[3-(1-hydroxymethyl-cyclopentyl)-propyl]-3-aza-bicyclo[3.1.0]hex-6-yl}-phenyl)-methanesulfonamide;

Exo-1-{3-[6-(3,5-difluoro-phenyl)-6-ethyl-3-aza-bicyclo[3.1.0]hex-3-yl]-propyl}-cyclohexanol;

Exo-3-{6-ethyl-3-[3-(1-hydroxy-cyclohexyl)-propyl]-3-aza-bicyclo[3.1.0]hex-6-yl}-benzamide;

Exo-2-methoxy-ethanesulfonic acid (3-{6-ethyl-3-[3-(1-hydroxy-cyclohexyl)-propyl]-3-aza-bicyclo[3.1.0]hex-6-yl}-phenyl)-amide;

Exo-2-methoxy-ethanesulfonic acid (3-{6-ethyl-3-[3-(1-hydroxy-cyclohexyl)-propyl]-3-aza-bicyclo[3.1.0]hex-6-yl}-phenyl)-amide citrate;

Exo-N-(3-{6-ethyl-3-[3-(1-hydroxy-cyclohexyl)-propyl]-3-aza-bicyclo[3.1.0]hex-6-yl}-5-fluoro-phenyl)-methanesulfonamide;

Exo-N-(3-{6-ethyl-3-[3-(1-hydroxy-cyclohexyl)-propyl]-3-aza-bicyclo[3.1.0]hex-6-yl}-5-fluoro-phenyl)-methanesulfonamide besylate;

Exo-3-{6-ethyl-3-[3-(1-hydroxy-cyclohexyl)-propyl]-3-aza-bicyclo[3.1.0]hex-6-yl}-5-fluoro-benzamide;

Exo-3-{6-ethyl-3-[3-(1-hydroxy-cyclohexyl)-propyl]-3-aza-bicyclo[3.1.0]hex-6-yl}-5-fluoro-benzamide tosylate Exo-1-methyl-1-H-imidazole-4-sulfonic acid (3-{6-ethyl-3-[3-(1-hydroxy-cyclohexyl)-propyl]-3-aza-bicyclo[3.1.0]hex-6-yl}-phenyl)-amide;

Exo-1-methyl-1-H-imidazole-4-sulfonic acid (3-{6-ethyl-3-[3-(1-hydroxy-cyclohexyl)-propyl]-3-aza-bicyclo[3.1.0]hex-6-yl}-phenyl)-amide citrate;

Exo-3-{6-ethyl-3-[3-(1-hydroxy-cyclohexyl)-propyl]-3-aza-bicyclo[3.1.0]hex-6-yl}-phenol;

Exo-3-{6-ethyl-3-[3-(1-hydroxy-cyclohexyl)-propyl]-3-aza-bicyclo[3.1.0]hex-6-yl}-phenol citrate;

Exo-3-[6-ethyl-3-(2-hydroxy-indan-2-ylmethyl)-3-aza-bicyclo[3.1.0]hex-6-yl]-5-fluoro-benzamide;

Exo-N-{3-[6-ethyl-3-(2-hydroxy-indan-2-ylmethyl)-3-aza-bicyclo[3.1.0]hex-6-yl]-phenyl}-methanesulfonamide;

Exo-N-{3-[6-ethyl-3-(2-hydroxy-indan-2-ylmethyl)-3-aza-bicyclo[3.1.0]hex-6-yl]-phenyl}-methanesulfonamide mesylate;

Exo-3-[6-ethyl-3-(2-hydroxy-indan-2-ylmethyl)-3-aza-bicyclo[3.1.0]hex-6-yl]-benzamide;

Exo-3-[6-ethyl-3-(2-hydroxy-indan-2-ylmethyl)-3-aza-bicyclo[3.1.0]hex-6-yl]-benzamide citrate;

Exo-2-methoxy-ethanesulfonic acid {3-[6-ethyl-3-(2-hydroxy-indan-2-ylmethyl)-3-aza-bicyclo[3.1.0]hex-6-yl]-phenyl}-amide;

Exo-N-{3-[6-ethyl-3-(2-hydroxy-indan-2-ylmethyl)-3-aza-bicyclo[3.1.0]hex-6-yl]-5-fluoro-phenyl}-methanesulfonamide;

Exo-1-methyl-1H-imidazole-4-sulfonic acid {3-[6-ethyl-3-(2-hydroxy-indan-2-ylmethyl)-3-aza-bicyclo[3.1.0]hex-6-yl]-phenyl}-amide;

Exo-2-[6-ethyl-6-(3-hydroxy-phenyl)-3-aza-bicyclo[3.1.0]hex-3-ylmethyl]-indan-2-ol;

Exo-2-methoxy-ethanesulfonic acid [3-(6-ethyl-3-indan-2-ylmethyl-3-aza-bicyclo[3.1.0]hex-6-yl)-phenyl]-amide;

Exo-3- (6-ethyl-3-indan-2-ylmethyl-3-aza-bicyclo[3.1.0]hex-6-yl)-benzamide;

Exo-1-methyl-1H-imidazole-4-sulfonic acid [3-(6-ethyl-3-indan-2-ylmethyl-3-aza-bicyclo[3.1.0]hex-6-yl)-phenyl]-amide; and Exo-3-(6-ethyl-3-indan-2-ylmethyl-3-aza-bicyclo[3.1.0]hex-6-yl)-phenol.

Preferred compounds of formula I of the invention are:

Exo-N-(3-{6-ethyl-3-[3-(1-hydroxy-cyclohexyl)-propyl]-3-aza-bicyclo[3.1.0]hex-6-yl}-phenyl)-methanesulfonamide;

Exo-N-(3-{6-ethyl-3-[3-(1-hydroxy-cyclohexyl)-propyl]-3-aza-bicyclo[3.1.0]hex-6-yl}-phenyl)-methanesulfonamide citrate Exo-N-(3-{6-ethyl-3-[3-(1-hydroxymethyl-cyclopentyl)-propyl]-3-aza-bicyclo[3.1.0]hex-6-yl}-phenyl)-methanesulfonamide;

Exo-N-(3-{6-ethyl-3-[3-(1-hydroxy-cyclohexyl)-propyl]-3-aza-bicyclo[3.1.0]hex-6-yl}-5-fluoro-phenyl)-methanesulfonamide;

Exo-N-(3-{6-ethyl-3-[3-(1-hydroxy-cyclohexyl)-propyl]-3-aza-bicyclo[3.1.0]hex-6-yl}-5-fluoro-phenyl)-methanesulfonamide besylate;

Exo-3-{6-ethyl-3-[3-(1-hydroxy-cyclohexyl)-propyl]-3-aza-bicyclo[3.1.0]hex-6-yl}-5-fluoro-benzamide;

Exo-3-{6-ethyl-3-[3-(1-hydroxy-cyclohexyl)-propyl]-3-aza-bicyclo[3.1.0]hex-6-yl}-5-fluoro-benzamide tosylate;

Exo-N-{3-[6-ethyl-3-(2-hydroxy-indan-2-ylmethyl)-3-aza-bicyclo[3.1.0]hex-6-yl]-phenyl}-methanesulfonamide;

Exo-N-{3-[6-ethyl-3-(2-hydroxy-indan-2-ylmethyl)-3-aza-bicyclo[3.1.0]hex-6-yl]-phenyl}-methanesulfonamide mesylate;

Exo-2-methoxy-ethanesulfonic acid {3-[6-ethyl-3-(2-hydroxy-indan-2-ylmethyl)-3-aza-bicyclo[3.1.0]hex-6-yl]-phenyl}-amide;

Exo-2-methoxy-ethanesulfonic acid (3-{6-ethyl-3-[3-(1-hydroxy-cyclohexyl)-propyl]-3-aza-bicyclo[3.1.0]hex-6-yl}-phenyl)-amide;

Exo-3-[6-ethyl-3-(2-hydroxy-indan-2-ylmethyl)-3-aza-bicyclo[3.1.0]hex-6-yl]-benzamide;

Exo-3-[6-ethyl-3-(2-hydroxy-indan-2-ylmethyl)-3-aza-bicyclo[3.1.0]hex-6-yl]-benzamide citrate;

Exo-3-{6-ethyl-3-[3-(1-hydroxy-cyclohexyl)-propyl]-3-aza-bicyclo[3.1.0]hex-6-yl}-phenol;

Exo-3-{6-ethyl-3-[3-(1-hydroxy-cyclohexyl)-propyl]-3-aza-bicyclo[3.1.0]hex-6-yl}-phenol citrate;

Exo-2-[6-ethyl-6-(3-hydroxy-phenyl)-3-aza-bicyclo[3.1.0]hex-3-ylmethyl]-indan-2-ol Exo-3-{6-Ethyl-3-[2-(2-hydroxy-indan-2-yl)-ethyl]-3-aza-bicyclo[3.1.0]hex-6-yl}-benzamide;

(+/−)-exo-2-Methoxy-ethanesulfonic acid {3-[6-ethyl-3-(2-hydroxy-1,2,3,4-tetrahydro-naphthalen-2-ylmethyl)-3-aza-bicyclo[3.1.0]hex-6-yl]-phenyl}-amide;

(+)-exo—N-{3-[6-Ethyl-3-(2-hydroxy-1,2,3,4-tetrahydro-naphthalen-2-ylmethyl)-3-aza-bicyclo[3.1.0]hex-6-yl]-phenyl}-methanesulfonamide;

(−)-exo—N-{3-[6-Ethyl-3-(2-hydroxy-1,2,3,4-tetrahydro-naphthalen-2-ylmethyl)-3-aza-bicyclo[3.1.0]hex-6-yl]-phenyl}-methanesulfonamide;

Exo-3-[3-(2-Hydroxy-indan-2-ylmethyl)-6-propyl-3-aza-bicyclo[3.1.0]hex-6-yl]-benzamide;

Exo-3-{3-[3-(1-Hydroxy-cyclohexyl)-propyl]-6-propyl-3-aza-bicyclo[3.1.0]hex-6-yl}-benzamide;

Exo-N-(3-{3-[3-(1-Cyano-cyclohexyl)-propyl]-6-ethyl-3-aza-bicyclo[3.1.0]hex-6-yl}-phenyl)-methanesulfonamide;

Exo-2-Methoxy-ethanesulfonic acid {3-[3-(2-hydroxy-indan-2-ylmethyl)-6-propyl-3-aza-bicyclo[3.1.0]hex-6-yl]-phenyl}-amide;

Exo-N-{3-[3-(2-Hydroxy-indan-2-ylmethyl)-6-isopropyl-3-aza-bicyclo[3.1.0]hex-6-yl]-phenyl}-methanesulfonamide;

Exo-2-Methoxy-ethanesulfonic acid (3-{3-[3-(1-hydroxy-cyclohexyl)-propyl]-6-isopropyl-3-aza-bicyclo[3.1.0]hex-6-yl}-phenyl)-amide;

Exo-N-{3-[6-Ethyl-3-(cis-1-hydroxy-3-phenyl-cyclobutyl methyl)-3-aza-bicyclo[3.1.0]hex-6-yl]-phenyl}-methanesulfonamide;

Exo-3-[6-Ethyl-3-(cis-1-hydroxy-3-phenyl-cyclobutylmethyl)-3-aza-bicyclo[3.1.0]hex-6-yl]-benzamide;

Exo-Ethanesulfonic acid {3-[6-ethyl-3-(2-hydroxy-indan-2-ylmethyl)-3-aza-bicyclo[3.1.0]hex-6-yl]-phenyl}-amide; and Exo-Ethanesulfonic acid (3-{6-ethyl-3-[3-(1-hydroxy-cyclohexyl)-propyl]-3-aza-bicyclo[3.1.0]hex-6-yl}-phenyl)-amide;

and, of the above compounds that are not salt forms, pharmaceutically acceptable salts thereof.

The term "alkyl" as used herein unless otherwise indicated includes saturated monovalent hydrocarbon radicals having straight or branched moieties. Examples of alkyl groups include, but are not limited to, methyl, ethyl, propyl, isopropyl, and t-butyl.

The term "cycloalkyl" as used herein unless otherwise indicated includes non-aromatic saturated cyclic alkyl moieties wherein alkyl is as defined above. Examples of cycloalkyl include, but are not limited to, cyclopropyl, cyclobutyl, cyclopentyl, cyclohexyl, and cycloheptyl.

The term "aryl" as used herein unless otherwise indicated includes an organic radical derived from an aromatic hydrocarbon by removal of one hydrogen, such as phenyl, naphthyl, indenyl, and fluorenyl.

The term "heteroaryl" as used herein unless otherwise indicated refers to aromatic groups containing one or more heteroatoms (O, S, or N), preferably from one to four heteroatoms. A multicyclic group containing one or more heteroatoms wherein at least one ring of the group is aromatic is a "heteroaryl" group. The heteroaryl groups of this invention can also include ring systems substituted with one or more oxo moieties. Examples of heteroaryl groups are pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, indolyl, benzimidazolyl, benzofuranyl, cinnolinyl, indazolyl, indolizinyl, phthalazinyl, triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl.

The foregoing groups, as derived from the compounds listed above, may be C-attached or N-attached where such is possible. For instance, a group derived from pyrrole may be pyrrol-1-yl (N-attached) or pyrrol-3-yl (C-attached). The terms referring to the groups also encompass all possible tautomers.

Salts of compounds of Formula I can be obtained by forming salts with any acidic or basic group present on a compound of Formula I. Examples of pharmaceutically acceptable salts of the compounds of Formula I are the salts of hydrochloric acid, p-toluenesulfonic acid, fumaric acid, citric acid, succinic acid, salicylic acid, oxalic acid, hydrobromic acid, phosphoric acid, methanesulfonic acid, tartaric acid, maleic acid, di-p-toluoyl tartaric acid, acetic acid, sulfuric acid, hydroiodic acid, mandelic acid, sodium, potassium, magnesium, calcium, and lithium.

In a preferred practice, the compounds of Formula I subject of the invention are in salt form.

The compounds of Formula I may have optical centers and therefore may occur in different enantiomeric and other stereoisomeric configurations. The azabicyclohexanes subject of the inventive process include all enantiomers, diastereomers, and other stereoisomers of such compounds of Formula I, as well as racemic and other mixtures thereof.

Impurities:

The present process reduces impurities in the preparation of azabicyclohexane compounds. The use of the plural and singular herein regarding impurities and otherwise is interchangeable. The "at least one process-related impurity" and the like as used herein include those impurities appreciated by the artisan as associated with the synthesis of azabicylco [3.1.0]hexane compounds, 3-azabicyclo[3.1.0]hexane compounds in particular. These typically include without limitation, polar impurities such as oxygen- and sulfur-containing compounds and the like. A particular impurity subject to the present process are the ethers, especially THF as aforesaid; or process-related impurities having another ether moiety, e.g. a methyl ether. Other impurities include residue of other solvents used in the manufacturing process, e.g. 2-propanol at times. Still other impurities subject of the invention are those associated with azabicyclo[3.1.0]hexanes as polar by-products of reaction. The practice of the present invention reduces the amount of impurity from a first concentration to a second, lower concentration, e.g. a reduction in the concentration of THF from one that is clinically unacceptable to one that is.

The process of the invention comprises contacting a mixture that contains said azabicyclo[3.1.0]hexane and said process-related impurity with a solvent comprising an alcohol, such as lower alkanols e.g. methanol, ethanol, propanol (e.g. 2-propanol). In a first preferred embodiment, said alcohol is ethanol, more preferably absolute ethanol; this first embodiment is especially utile when said process-related impurity is THF. In a second preferred embodiment, said alcohol is methanol; this second embodiment is especially utile when said process-related impruity has an ether moety such as a methyl ether moiety. In another embodiment, the solvent comprises alcohol as aforesaid and water, preferably in an alcohol:water ratio (volume/volume, v/v) of at least about 85:15, more preferably at least about 90:10; still more preferably at least about 95:5. Variations on this practice are contemplated as within the scope of invention and will be understood as such by the artisan. For example, the contacting can be cascaded; or multiple contacting steps can be employed using e.g. the product generated by the process, thus exposing the azabicyclo[3.1.0]hexane-containing mixture to repeated cycling through the process with commensurate reductions in impurity.

Constitution of the solvent may also vary within the parameters aforesaid, thus alcohol may be used in one cascade or cycle and an alcohol:water solvent may be used in another, with reverse and other permutations and combinations being within operational ambit. While contacting may occur at a wide range of temperatures, e.g. about 0° C. to about 82° C., is preferably performed at elevated temperature, i.e. greater than ambient (>−25° C.); in a particularly preferred practice, contacting is at reflux temperature, e.g. reflux temperature for ethanol solvent practice is ~72° C.; for methanol, reflux temperature is ~66° C.

Quantitatively, the volume of solvent (e.g. alcohol) to azabicyclo[3.1.0]hexane/impurity mixture used in the process is sufficient to generate a slurry; without limitation, up to about 12 volumes of solvent (e.g. alcohol) are typically used per unit volume of azabicyclo[3.1.0]hexane/impurity mixture; preferably, about 8 to about 12 volumes are used; more preferably, about 10 volumes solvent for each volume of azabicyclo[3.1.0]hexane/impurity mixture to be processed.

Contacting is for an amount of time adequate to reduce levels of impurity as desired and depends in part on the volumes and concentrations involved as will be understood to the artisan; generally, for bulk quantities (e.g. > about 1–10 Kg) contacting is preferably for at least about 1 hr; more preferably about 1 to about 4 hr. Contacting may be without or (preferably) with agitation, e.g. by stirrer or other means known in the art.

In one embodiment, the mixture containing the azabicyclo [3.1.0]hexane compound with one or more process-related impurities is combined with said solvent, the slurry that results is then heated to e.g. reflux temperature for a period of about at least 0.5 hr, preferably about 1 hr, with stirring. Recovery may be accomplished by means known in the art, including without limitation e.g. filtration, drying, granulation and the like.

The following examples are illustrative of the present process; they are not to be construed as limiting the scope or practice of same.

EXAMPLE 1

This example demonstrates an embodiment of the process of the invention wherein an azabicyclohexane having at least THF impurity is slurried with refluxing absolute ethanol, cooled and filtered with the solids recovered having less THF.

An azabicyclo[3.1.0]hexane salt compound was prepared as described in patent application U.S. Ser. No. 10/278,142 and isolated as crude bulk (1.5 Kg; 82% yield; 97.7% purity). Headspace analysis indicated this material had at least the following impurities: 1.4% THF; 0.6 % 2-propanol; and 0.4% unreacted residual substrate (polar). Further drying at 50° C. did little to remove these materials, especially the THF levels.

To a speck-free 22 liter round bottom flask was charged 1.5 Kg of the azabicyclo[3.1.0]hexane crude bulk aforesaid and 9 liters of absolute ethanol. The resulting slurry was heated to reflux and stirred at reflux for 1 hour. The slurry was then cooled to 10° C. and granulated for 1 hour. Whereafter, solids were filtered off and washed with 1 liter of cold absolute ethanol, then vacuum dried at 50° C. overnight. The solids were then hand sieved through an 18 mesh screen. This resulted in the isolation of 1.4 Kg (75.6% yield) of azabicyclo[3.1.0]hexane. Headspace analysis showed 0.15% THF; 0.08% 2-propanol; 0.13% unreacted residual substrate; and 0.05% ethanol.

Thus in the practice of the invention THF impurity was reduced from 1.4% to 0.15%; 2-propanol was reduced from 0.6% to 0.08%; and unreacted residual substrate was reduced from 0.4% to 0.13%. Overall purity was also raised form 97.7% to 99.1%.

Yield was 75.6%.

EXAMPLE 2

This example demonstrates another embodiment of the process of the invention using multiple cycles wherein an azabicyclo[3.1.0]hexane having at least THF impurity is slurried with refluxing ethanol:water (ratio of ethanol:water=95:5), cooled and filtered with the solids recovered having less THF.

An azabicyclo[3.1.0]hexane salt compound was prepared as described in patent application U.S. Ser. No. 10/278,142 and isolated as crude bulk (3.03 Kg; 76% yield; 94% purity). Headspace analysis indicated this material had at least the following impurities: 1.5% THF; 0.9 % 2-propanol; 1.3% unreacted residual substrate; and two additional polar impurities denominated MP at 1.2% and LP at 1.8%. (The MP impurity was more polar than the LP).

This crude bulk was subjected to the same process as described in Example 1. Headspace analysis showed 0.08% THF; 0.0% 2-propanol; 0.4% unreacted residual substrate; 0.3% MP impurity; and 0.4% LP impurity. Overall purity of this first cycle product was 98.9%.

The resulting product of this first cycle (98.9% purity) was then subjected to a second cycle using the process described in Example 1. Headspace analysis showed 0% THF; 0% 2-propanol; 0.3% unreacted residual substrate; <0.1% MP impurity; and 0.3% LP impurity. Overall purity of this second cycle product was 99%.

The resulting product of this second cycle (99% purity) was then subjected to a third cycle using the process described in Example 1 except for the fact that instead of absolute ethanol, an ethanol:water solvent was used (ethanol:water ratio=95:5) Headspace analysis showed 0% THF; 0% 2-propanol; <0.05% unreacted residual substrate; 0% MP impurity; and 0.09% LP impurity. Overall purity of this third cycle product as 99.8%.

All material percentages in Examples 1 and 2 was from gradient reverse phase HPLC analysis.

EXAMPLE 3

This example demonstrates another embodiment of the process of the invention wherein an azabicyclo[3.1.0]hexane having a process-related impurity comprising a methyl ether moiety is slurried with refluxing methanol, cooled and filtered with the solids having less of said impurity.

An azabicyclo[3.1.0]hexane salt compound was prepared as described in patent application U.S. Ser. No. 10/278,142 and isolated as crude bulk (5.7 Kg; 76% yield). A process-related impurity containing a methyl ether moiety was identified in the crude bulk and found by High Performance Liquid Chromatography (HPLC) to be present at 1.6–1.8%.

To the 5.7 Kg (1 volume) of crude bulk was charged 6 volumes of methanol. The resulting slurry was heated to reflux, and held there while stirred for 1 hour. The slurry was then cooled to ambient temperature and filtered to isolate solids. The filter cake was washed with cold methanol, then dried. The dried solids weighed 4.7 Kg (82% mass recovery). HPLC analysis showed said impurity level to be 0.25–0.26%, down from the initial 1.6–1.8% level. No residual solvents were detected.

What is claimed is:

1. A purification process for an azabicyclo[3.1.0]hexane compound having reduced impurities comprising contacting a mixture containing an azabicyclo[3.1.0]hexane compound and at least one process-related impurity at a first concentration with an alcohol; and recovering from said mixture said azabicyclo[3.1.0]hexane compound having said at least one process-related impurity at a second concentration, said second concentration being less than said first concentration.

2. The process of claim 1 wherein said azabicyclo[3.1.0]hexane compound is a 3-azabicyclo[3.1.0]hexane compound.

3. The process of claim 2 wherein said 3-azabicyclo[3.1.0]hexane compound has the formula:

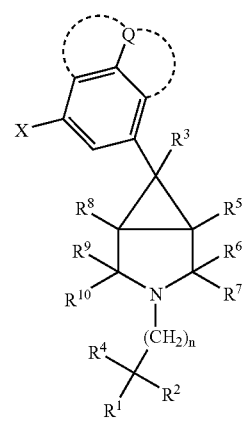

I wherein X is H, halogen, —OH, —CN, —$C_1$–$C_4$ alkyl substituted with from one to three halogen atoms, or —O($C_1$–$C_4$ alkyl), wherein the $C_1$–$C_4$ alkyl of —O($C_1$–$C_4$ alkyl) is optionally substituted with from one to three halogen atoms;

Q is halogen, —OH, —O($C_1$–$C_4$ alkyl), —$NH_2$, —NH($C_1$–$C_4$ alkyl), —N($C_1$–$C_4$ alkyl)($C_1$–$C_4$ alkyl), —C(=O)$NH_2$, —C(=O)NH($C_1$–$C_4$ alkyl), —C(=O)N($C_1$–$C_4$ alkyl)($C_1$–$C_4$ alkyl), —NHS(=O)$_2$H, or —NHS(=O)$_2R^{11}$;

or Q may form a 5 or 6 membered cycloalkyl or heterocycloalkyl ring with either carbon atom adjacent to the carbon atom to which it is attached, thereby forming a bicyclic fused ring system with the phenyl to which it is attached, wherein said heterocycloalkyl comprises from one to three hetero moieties selected from O, S, —C(=O), and N, and wherein said cycloalkyl or heterocycloalkyl optionally contains one or two double bonds;

$R^1$ and $R^2$ are, with the carbon to which they are attached, connected to form a $C_3$–$C_7$ cycloalkyl or a 4–7 membered heterocycloalkyl comprising from one to three hetero moieties selected from O, S, —C(=O), and N; and wherein said cycloalkyl or heterocycloalkyl optionally contains one or two double bonds; and wherein said cycloalkyl or heterocycloalkyl is optionally fused to a $C_6$–$C_{14}$ aryl or 5–14 membered heteroaryl group;

wherein said $C_3$–$C_7$ cycloalkyl or 4–7 membered heterocycloalkyl formed by $R^1$ and $R^2$ can each optionally be substituted by from one to three $R^{12}$ groups, and said optionally fused aryl or heteroaryl can each optionally independently be substituted with from one to six $R^{12}$ groups, wherein the $R^{12}$ groups are selected from $R^{13}$, $R^{16}$, —$C_1$–$C_4$ alkyl containing one or two unsaturated bonds, halogen, —$OR^{13}$, —$NO_2$, —CN, —$C_3$–$C_6$ cycloalkyl, —$NR^{13}R^{14}$, —$NR^{13}C(=O)R^{14}$, —C(=O)$NR^{13}R^{14}$, —OC(=O)$R^{13}$, —C(=O)$R^{13}$, —C(=O)$R^{13}$, —$NR^{13}C(=O)OR^{14}$, —$NR^{13}C(=O)NR^{14}R^{15}$, —$NR^{13}S(=O)_2R^{14}$, and —$S(=O)_2R^{13}$;

$R^3$ is $C_1$–$C_4$ alkyl, wherein said $C_1$–$C_4$ alkyl optionally contains one or two unsaturated bonds;

$R^4$ is —$C_1$–$C_4$ alkyl which may optionally contain one or two unsaturated bonds, —OH, —CN, $NO^2$, —$OR^{16}$, —$NH_2$, —$NHR^{16}$, —$NR^{16}R^{17}$, or —$NHC(=O)R^{16}$;

$R^5$ and $R^8$ are each independently H or methyl;

$R^6$ $R^7$, $R^9$ and $R^{10}$ are H;

$R^{11}$ is selected from $C_1$–$C_4$ alkyl, —($C_1$–$C_4$ alkylene)-O—($C_1$–$C_4$ alkyl), 4-(1-methylimidazole), —($C_1$–$C_4$ alkylene)—$NH_2$, —($C_1$–$C_4$ alkylene)-NH($C_1$–$C_4$ alkyl), —($C_1$–$C_4$ alkylene)-N($C_1$–$C_4$ alkyl)($C_1$–$C_4$ alkyl);

each $R^{13}$, $R^{14}$, and $R^{15}$ is independently selected from H, $R^{16}$, $C_1$–$C_4$ alkyl, halogen, —OH, —SH, —$NH_2$, —NH($C_1$–$C_4$ alkyl), —N($C_1$–$C_4$ alkyl)($C_1$–$C_4$ alkyl), —O($C_1$–$C_4$ alkyl), —S($C_1$–$C_4$ alkyl), —CN, —$NO_2$, —C(=O)($C_1$–$C_4$ alkyl), —C(=O)OH, —C(=O)O($C_1$–$C_4$ alkyl), —NHC(=O)($C_1$–$C_4$ alkyl), —C(=O)$NH_2$, and —C(=O)N($C_1$–$C_4$ alkyl)($C_1$–$C_4$ alkyl), or $R^{13}$ and $R^{14}$ when in —$NR^{13}R^{14}$, may optionally be connected to form a 4 to 6 membered heterocycloalkyl or heteroaryl group, which heterorayl group optionally comprises from 1 to 3 further hetero moieties selected from N, S, O and —C(=O);

each $R^{16}$ and $R^{17}$ is independently selected from $C_1$–$C_4$ alkyl, $C_6$–$C_{14}$ aryl and 5–14 membered heteroaryl, wherein said heteroaryl comprises from one to three hetero moieties selected from O, S, —C(=O), and N, and wherein said aryl and heteroaryl are optionally substituted with from one to three substituents selected from $C_1$–$C_4$ alkyl optionally containing one or two unsaturated bonds, halogen, —OH, —SH, —$NH_2$, —NH($C_1$–$C_4$ alkyl), —N($C_1$–$C_4$ alkyl)($C_1$–$C_4$ alkyl), —O($C_1$–$C_4$ alkyl), —S($C_1$–$C_4$ alkyl), —CN, —$NO_2$, —C(=O)($C_1$–$C_4$ alkyl), —C(=O)OH, —C(=O)O($C_1$–$C_4$ alkyl), —NHC(=O)($C_1$–$C_4$ alkyl), —C(=O)$NH_2$, and —C(=O)N($C_1$–$C_4$ alkyl)($C_1$–$C_4$ alkyl); and n is an integer selected from zero, 1, 2, 3, 4, and 5;

or a pharmaceutically acceptable salt thereof.

4. The process of claim 1 wherein said at least one process-related impurity is an oxygen-containing compound.

5. The process of claim 4 wherein said at least one process-related impurity is an ether.

6. The process of claim 5 wherein said ether is THF.

7. The process of claim 1 wherein said alcohol is ethanol.

8. The process of claim 5 wherein said ether is a methyl ether.

9. The process of claim 8 wherein said alcohol is methanol.

10. The process of claim 1 wherein said alcohol further comprises water.

11. The process of claim 10 wherein said alcohol and said water are present in a ratio of at least about 85:15.

12. The process of claim 1 wherein said contacting is at elevated temperature and said recovering is at a temperature below ambient.

13. A purification process for an azabicyclo[3.1.0]hexane compound comprising:
(a) contacting at elevated temperature a mixture of an azabicyclo[3.1.0]hexane compound and at least one process-related impurity, with a solvent comprising ethanol;
(b) cooling the product of (a) to below ambient temperature;
(c) recovering said azabicyclo[3.1.0]hexane compound from the product of (b)
wherein said process-related impurity is present in said recovered azabicyclo[3.1.0]hexane compound at a reduced concentration.

14. The process of claim 13 wherein said elevated temperature is at or about reflux temperature.

15. The process of claim 13 wherein said solvent further comprises water.

16. The process of claim 14 wherein said ethanol:water ratio is about 90:10 to about 99:1.

17. The process of claim 13 wherein step (a) further comprises agitating said mixture.

18. The process of claim 17 wherein said recovering step (c) comprises filtering the product of step (b) to obtain solids comprising said azabicyclo[3.1.0]hexane compound.

19. The process of claim 18 wherein said recovering step (c) further comprises washing said solids with additional solvent comprising ethanol.

20. The process of claim 19 wherein said recovering step (c) further comprises drying said washed solids at elevated temperature.

21. A purification process for an azabicyclo[3.1.0]hexane salt compound for therapeutic use comprising:
(a) contacting a mixture of an azabicyclo[3.1.0]hexane salt compound having THF at a first concentration, with a solvent comprising ethanol and optionally water;
(b) heating the product of step (a) to reflux optionally with agitation;
(c) granulating the product of step (b) at a temperature below ambient; and
(d) recovering said azabicyclo[3.1.0]hexane salt compound from the product of step (c), said recovered azabicyclo[3.1.0]hexane salt compound being in solids form and having THF at a reduced concentration compatible with therapeutic use.

* * * * *